(12) United States Patent
Ochoa et al.

(10) Patent No.: US 8,167,640 B2
(45) Date of Patent: May 1, 2012

(54) FLEXIBLE CONNECTOR FOR IMPLANTABLE ELECTRICAL STIMULATION LEAD

(75) Inventors: Francisco Ochoa, Cudahy, CA (US); Timothy Raymond Odell, Los Angeles, CA (US); Jeryle Walter, Valencia, CA (US)

(73) Assignee: Bioness Inc., Valencia, CA (US)

( * ) Notice: Subject to any disclaimer, the term of this patent is extended or adjusted under 35 U.S.C. 154(b) by 259 days.

(21) Appl. No.: 12/407,097

(22) Filed: Mar. 19, 2009

(65) Prior Publication Data

US 2010/0240240 A1    Sep. 23, 2010

(51) Int. Cl.
    *H01R 13/64* (2006.01)
(52) U.S. Cl. ............ 439/379; 439/909; 607/37; 607/57; 607/116; 600/378
(58) Field of Classification Search .................. 439/378, 439/379, 380, 909; 607/37, 38, 57, 116, 607/137; 600/378
    See application file for complete search history.

(56) References Cited

U.S. PATENT DOCUMENTS

| | | | |
|---|---|---|---|
| 4,166,469 A | 9/1979 | Littleford | |
| 4,342,498 A * | 8/1982 | Patton et al. | 439/839 |
| 4,469,104 A | 9/1984 | Peers-Trevarton | |
| 4,880,401 A * | 11/1989 | Shima et al. | 439/746 |
| 4,898,183 A | 2/1990 | Kuzma | |
| 5,003,990 A | 4/1991 | Osypka | |
| 5,070,605 A | 12/1991 | Daglow et al. | |
| 5,170,787 A | 12/1992 | Lindegren | |
| 5,350,318 A | 9/1994 | Nees | |
| 5,439,464 A | 8/1995 | Shapiro | |
| 5,476,399 A * | 12/1995 | Porter | 439/843 |
| 5,667,514 A | 9/1997 | Heller | |
| 5,782,841 A | 7/1998 | Ritz et al. | |
| 5,788,542 A * | 8/1998 | Miwa | 439/851 |
| 5,791,944 A | 8/1998 | Grant et al. | |
| 5,984,890 A | 11/1999 | Gast et al. | |
| 6,149,657 A | 11/2000 | Kuzma | |
| 6,185,464 B1 | 2/2001 | Bonner et al. | |
| 6,304,785 B1 | 10/2001 | McCreery et al. | |
| 6,530,929 B1 | 3/2003 | Justis et al. | |
| 6,605,094 B1 | 8/2003 | Mann et al. | |
| 6,662,035 B2 | 12/2003 | Sochor | |
| 6,697,677 B2 | 2/2004 | Dahl et al. | |
| 6,829,508 B2 | 12/2004 | Schulman et al. | |

(Continued)

OTHER PUBLICATIONS

International Search Report and Written Opinion for International Application No. PCT/US2010/026891, mailed May 19, 2010, 11 pages.

*Primary Examiner* — James Harvey
(74) *Attorney, Agent, or Firm* — Cooley LLP

(57) ABSTRACT

In some embodiments, an apparatus includes an electrical connector having a side wall defining a lumen and an elongate opening. The lumen is configured to receive at least a conductive portion of an electronic implant. The elongate opening divides the side wall into a first portion and a second portion. The first portion of the side wall is configured to move relative to the second portion of the side wall between a first position and a second position. The first portion of the side wall is electrically conductive and includes a protrusion. The protrusion is configured to contact the conductive portion of the electronic implant such that the conductive portion of the electronic implant is electrically coupled to the first portion of the side wall when the first portion of the side wall is in the second position.

21 Claims, 6 Drawing Sheets

U.S. PATENT DOCUMENTS

| | | |
|---|---|---|
| 6,835,084 B2 | 12/2004 | Poon et al. |
| 6,968,238 B1 | 11/2005 | Kuzma |
| 6,980,863 B2 | 12/2005 | van Venrooij et al. |
| 6,999,819 B2 | 2/2006 | Swoyer et al. |
| 7,018,384 B2 | 3/2006 | Skakoon |
| 7,050,858 B1 | 5/2006 | Kuzma et al. |
| 7,063,708 B2 | 6/2006 | Gibson et al. |
| 7,092,765 B2 | 8/2006 | Geske et al. |
| 7,094,064 B2 | 8/2006 | Sweetland et al. |
| 7,621,754 B2 * | 11/2009 | Costello .................. 439/65 |
| 2003/0028232 A1 | 2/2003 | Camps et al. |
| 2003/0139794 A1 | 7/2003 | Jenney et al. |
| 2003/0143895 A1 | 7/2003 | Sommer et al. |
| 2003/0199951 A1 | 10/2003 | Pardo et al. |
| 2005/0113894 A1 | 5/2005 | Zilberman et al. |
| 2005/0251237 A1 | 11/2005 | Kuzma et al. |
| 2006/0047321 A1 | 3/2006 | Biggs et al. |
| 2007/0078503 A1 | 4/2007 | Kuzma et al. |
| 2007/0156012 A1 | 7/2007 | Tracey et al. |
| 2009/0066352 A1 | 3/2009 | Gritters et al. |
| 2009/0076521 A1 | 3/2009 | Hansen |
| 2009/0182401 A1 | 7/2009 | Glukhovsky |
| 2009/0182402 A1 | 7/2009 | Glukhovsky |
| 2009/0182403 A1 | 7/2009 | Glukhovsky |
| 2010/0036465 A1 | 2/2010 | Glukhovsky et al. |
| 2010/0240240 A1 * | 9/2010 | Ochoa et al. .................. 439/207 |

* cited by examiner

FLEXIBLE CONNECTOR FOR IMPLANTABLE ELECTRICAL STIMULATION LEAD

BACKGROUND

The embodiments described herein relate generally to medical devices and, more particularly, to a flexible connector for removeably coupling an electrical stimulation lead to an electronic device.

Known electrical stimulation implants are used in various medical procedures. For example, some known electrical stimulation implants can be implanted within a patient's body to stimulate a response from a bodily organ or tissue, such as, for example, the heart, a muscle group or the like. Some known medical procedures include temporarily coupling a portion of an electrical stimulation implant to an electronic device during implantation to verify the placement of the implant within the body. For example, some known medical procedures include coupling a portion of a stimulation lead to a stimulator and supplying a current to the lead via the stimulator to validate the position of the implant within the body. During such procedures, however, the electronic device can be coupled to the electrical stimulation implant such that a conductive portion of the electrical stimulation implant can become damaged. As a result, the performance of the electrical stimulation implant can be compromised. Damage to the conductive portion can result from the pressure exerted by the device on the conductive portion of the implant.

Thus, a need exists for improved apparatus for removeably coupling an electrical stimulation implant to an electronic device.

SUMMARY

Medical devices are described herein. In some embodiments, an apparatus includes an electrical connector having a side wall defining a lumen and an elongate opening. The lumen is configured to receive at least a conductive portion of an electronic implant. The elongate opening divides the side wall into a first portion and a second portion. The first portion of the side wall is configured to move relative to the second portion of the side wall between a first position and a second position. The first portion of the side wall is electrically conductive and includes a protrusion. The protrusion is configured to contact the conductive portion of the electronic implant such that the conductive portion of the electronic implant is electrically coupled to the first portion of the side wall when the first portion of the side wall is in the second position.

DETAILED DESCRIPTION

Figure 1:
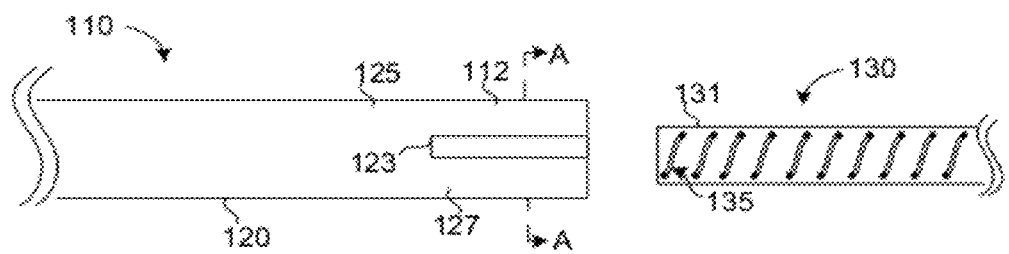
FIG. 1 is a schematic illustration of an electrical connector and an electronic implant according to an embodiment in a first configuration.

In some embodiments, an apparatus includes an electrical connector having a side wall defining a lumen and an elongate opening. The lumen is configured to receive at least a conductive portion of an electronic implant. The elongate opening divides the side wall into a first portion and a second portion. The first portion of the side wall is configured to move relative to the second portion of the side wall between a first position and a second position. The first portion of the side wall is electrically conductive and includes a protrusion. The protrusion is configured to contact the conductive portion of the electronic implant such that the conductive portion of the electronic implant is electrically coupled to the first portion of the side wall when the first portion of the side wall is in the second position. In some embodiments, the electrical connector is configured to convey an electrical signal between the electronic implant and an electronic device, such as, for example, a stimulator, via the first portion of the side wall when the protrusion is electrically coupled to the conductive portion of the electronic implant.

In some embodiments, an apparatus includes an electrical connector having a side wall that defines a lumen and an elongate opening. The lumen is configured to receive at least a conductive portion of an electronic implant. The elongate opening divides the side wall into a first portion and a second portion. The first portion of the side wall is configured to elastically or plastically deform when the first portion is moved relative to the second portion between a first position and a second position. Additionally, the first portion is configured to move from the first position to the second position when the conductive portion of the electronic implant is positioned adjacent the first portion. Moreover, the first portion is configured to exert a force, for example, between approximately 5 grams ($4.9 \times 10^{-2}$ N) and approximately 15 grams ($1.47 \times 10^{-1}$ N), on the conductive portion of the electronic implant when the first portion is in the second position. In some embodiments, the force prevents the electronic implant from moving relative to the electrical connector.

In some embodiments, a method includes inserting a portion of an electronic implant within a lumen defined by a side wall of an electrical conductor. In this manner, the conductive portion of the electronic implant is electrically coupled to a first portion of the side wall, which defines an elongate opening. The elongate opening divides the side wall into a first portion and a second portion. The first portion of the side wall is configured to elastically or plastically deform between a first portion and a second portion when the conductive portion is disposed within the lumen. A connection member is coupled to a proximal end portion of the electrical connector such that the electrical connector is electrically coupled to an external device via the connection member. In some embodiments, after the connection member is coupled to the electrical connector, an electrical signal is conveyed between the electrical connector and the electronic implant via the first portion of the side wall.

As used in this specification, the words "proximal" and "distal" refer to the direction closer to and away from, respectively, an operator (e.g., surgeon, physician, nurse, technician, etc.) who would use a medical device during a procedure. For example, the end of a medical device closest to the patient's body would be the distal end, while the opposite end of the medical device (e.g., the end of the medical device being operated by the operator) would be the proximal end of the medical device.

The term "electronic implant" as used herein can refer to either an implant including active electronic circuitry or an implant including a passive portion of an electronic circuit system, unless otherwise specified. For example, as used herein, an electronic implant can include active devices, such as microstimulators, amplifiers, power supplies, sensors or the like. An electronic implant can also include passive devices, such as passive conductors, leads, wires, or the like.

Figure 2:
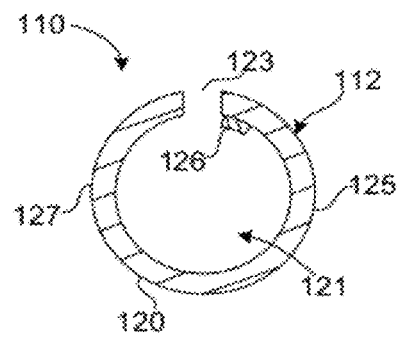
FIG. 2 is a cross-sectional view of the electrical connector shown in FIG. 1 taken along the line A-A.
Figure 3:
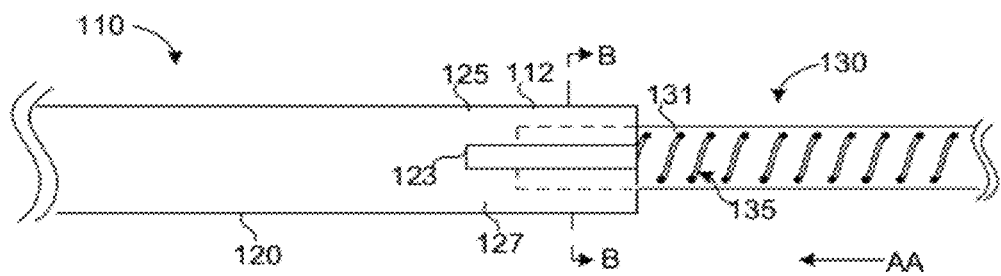
FIG. 3 is a schematic illustration of the electrical connector and the electronic implant shown in FIG. 1 in a second configuration.
Figure 4:
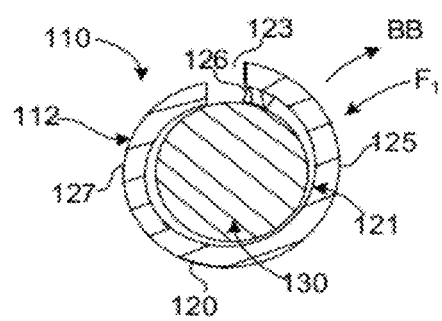
FIG. 4 is a cross-sectional view of the electrical connector and electronic implant shown in FIG. 3 taken along the line B-B.

FIGS. 1 and 3 are schematic illustrations of a distal end portion 112 of an electrical connector 110 and an electronic implant 130 according to an embodiment in a first configuration and a second configuration, respectively. Additionally, FIGS. 2 and 4 are cross-sectional views of the electrical connector 110 illustrated in FIGS. 1 and 3 taken along the lines A-A and B-B, respectively. The electrical connector 110, which can be constructed of, for example, metal tubing, includes a side wall 120. The side wall 120 defines a lumen 121 and an elongate opening 123. The lumen 121, which has a circular cross-section, is configured to receive a portion of the electronic implant 130. In some embodiments, the lumen 121 can have a non-circular cross-section. In some embodiments, the lumen 121 can extend through the entire length of the electrical connector 110. In other embodiments, however, the lumen 121 extends only through a portion of the length of the electrical connector 110.

The elongate opening 123, which can be, for example, a slit, divides the side wall 120 into a first portion 125 and a second portion 127. The elongate opening 123 extends longitudinally from the distal-most end of the distal end portion 112 of the electrical connector 110 toward a proximal end portion (not shown in FIGS. 1-4) of the electrical connector 110. Although the side wall 120 is illustrated and described as having a single elongate opening 123, in other embodiments, the side wall 120 can define more than one elongate opening to divide the side wall 120 into the first portion 125 and the second portion 127 or more portions (not illustrated).

The first portion 125 of the side wall 120 includes a protrusion 126 that is disposed within the lumen 121. The protrusion 126 is configured to contact a conductive portion 135 of the electronic implant 130 when the conductive portion 135 is disposed within the lumen 121, as described in more detail herein. Specifically, the first portion 125 of the side wall 120 and the protrusion 126 are collectively configured to be electrically coupled to the conductive portion 135 of the electronic implant 130 when the protrusion 126 is in contact with the conductive portion 135. In some embodiments, the first portion 125 and the protrusion 126 are constructed of an electrically conductive material such that the contact between the protrusion 126 and the conductive portion 135 of the electronic implant 130 results in the electrical coupling, as described herein.

The first portion 125 of the side wall 120 is configured to move relative to the second portion 127 of the side wall 120 between a first position (e.g., FIG. 2) and a second position (e.g., FIG. 4). Specifically, at least the first portion 125 of the side wall 120 is flexible such that the first portion 125 can move between the first position and the second position. In some embodiments, the first portion 125 of the side wall 120 is configured to elastically deform when the first portion 125 moves from the first position to the second position. In other embodiments, however, the first portion 125 of the side wall 120 is configured to plastically deform when the first portion 125 moves from the first position to the second position. Similarly stated, in some embodiments, the first portion 125 is configured to move irreversibly from the first position to the second position.

When the electrical connector 110 is in the first configuration, as shown in FIGS. 1 and 2, the electronic implant 130 is disposed outside the lumen 121 and the first portion 125 of the side wall 120 is in the first position. When the first portion 125 is in the first position, the side wall 120 of the electrical connector 110 has a substantially circular cross-section. Specifically, the first portion 125 of the side wall 120 has an orientation relative to the second portion 127 of the side wall 120 such that the first portion 125 and the second portion 127 collectively form a substantially circular cross-section when the first portion 125 is in the first position, as shown in FIG. 2. In some embodiments, however, the first portion 125 of the side wall 120 can have an orientation relative to the second portion 127 such that the side wall 120 has a substantially non-circular cross-section when the first portion 125 is in the first position. For example, when the first portion 125 is in the first position, the side wall 120 can have an oval shape, a square shape, and/or any other shape.

When the electrical connector 110 is in the second configuration, as shown in FIGS. 3 and 4, at least a proximal end portion 131 of the electronic implant 130 is disposed within the lumen 121. The electronic implant 130 can be inserted into the lumen 121 by moving the electronic implant 130 longitudinally in a direction AA toward the lumen 121. Said another way, when the electrical connector 110 is in the second configuration, the lumen 121 defined by the side wall 120 receives at least a proximal end portion 131 of the electronic implant 130.

When the electronic implant 130 is disposed within the lumen 121, the protrusion 126 of the first portion 125 of the side wall 120 contacts a conductive portion 135 of the electronic implant 130. As a result of the contact between the protrusion 126 and the conductive portion 135, the first portion 125 of the side wall 120 is moved from the first position into the second position. Specifically, as shown in FIG. 4, the electronic implant 130 has an outer diameter substantially the same as an inner diameter of the lumen 121 (shown in FIG. 2) such that the first portion 125 of the side wall 120 moves in an outward direction BB when the protrusion 126 contacts the conductive portion 135 of the electronic implant 130. Said another way, the contact between the protrusion 126 and the conductive portion 135 causes the first portion 125 of the side wall 120 to move in the direction BB when the proximal end 131 of the electronic implant 130 is disposed within the lumen 121. In this manner, the first portion 125 of the side wall 120 moves relative to the second portion 127 of the side wall 120 from the first position to the second position when the proximal end portion 131 of the electronic implant 130 is disposed within the lumen 121.

As shown in FIG. 4, the first portion 125 of the side wall 120 exerts a force $F_1$ on the conductive portion 135 of the electronic implant 130 via the protrusion 126 when the electrical connector 110 is in the second configuration. In this manner, the force $F_1$ on the conductive portion 135, which is in a direction opposite to that of direction BB, can retain the proximal end portion 131 of the conductive portion 135 within the lumen 121. In some embodiments, the magnitude of the force $F_1$ can be sufficient to limit the longitudinal and/or rotational movement of the electronic implant 130 within the lumen 121. In some embodiments, the magnitude of the force $F_1$ can be sufficient to elastically deform the conductive portion 135 of the electronic implant 130 that is in contact with the protrusion 126. As described in more detail herein, the magnitude of the force $F_1$ can correspond to the material properties and/or the dimensions of the side wall 120 of the electrical connector 110.

When the electrical connector 110 is in the second configuration, the first portion 125 is electrically coupled to the conductive portion 135 of the electronic implant 130 via the protrusion 126. More particularly, the force $F_1$ exerted on the conductive portion 135 by the first portion 125 via the protrusion 126 facilitates the electrical coupling of the first portion 125 and the conductive portion 135. In this manner, an electrical signal can be conveyed between the first portion 125 and the electronic implant 130 via the protrusion 126. In some such embodiments, an external device (not shown) can be coupled to a proximal end portion of the electrical connector 110 such that the external device is electrically coupled to the electronic implant 130 via the protrusion 126 and the first portion 125 of the side wall 120. In this manner, an electrical signal can be conveyed between the external device and the electronic implant 130. In some such embodiments, the external device can be, for example, a voltmeter, ammeter, pulse generator, stimulator and/or any other suitable device.

In some embodiments, the electronic implant 130 includes an outer, non-conductive sheath (not shown), which substantially surrounds the conductive portion 135 of the electronic implant 130. The outer sheath can include an opening such that the protrusion 126 can fit within the opening and directly contact the conductive portion 135 of the electronic implant 130. In this manner, the protrusion 126 can electrically couple to the conductive portion 135 of the electronic implant 130 via the opening in the sheath.

The first portion 125 of the side wall 120 and the protrusion 126 can be coupled together by any suitable means. For example, the first portion 125 of the side wall 120 and the protrusion 126 can be coupled together by a mechanical coupling (e.g., an interference fit, a threaded coupling, or the like), an electronic coupling (e.g., a magnetic coupling), and/or a chemical bond. In some embodiments, however, the first portion 125 of the side wall 120 and the protrusion 126 can be monolithically constructed. Although the protrusion 126 is shown as being coupled to a distal-most portion of the first portion 125 of the side wall 120, in other embodiments, the protrusion 126 can be coupled in any suitable location along the first portion 125 of the side wall 120. Additionally, although the protrusion 126 is illustrated and described above as having a substantially rectangular cross-section, in some embodiments, the protrusion 126 can have any shape and/or size to facilitate contact with the conductive portion 135 of the electronic implant 130.

Although the elongate opening 123 is illustrated in FIGS. 1 and 3 as having a substantially rectangular shape, the elongate opening 123 can have any shape and/or size to facilitate the division of the side wall 120 into the first portion 125 and the second portion 127. Additionally, although the elongate opening 123 is illustrated in FIGS. 1 and 3 as extending from the distal-most end of the distal end portion 112 of the electrical connector 110, in some embodiments, the side wall 120 can define the elongate opening 123 at any location along the electrical connector 110, as described herein.

Figure 5:
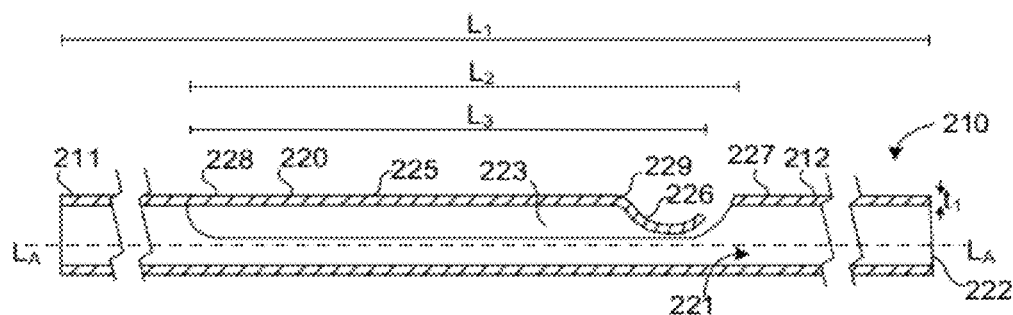
FIG. 5 is a cross-sectional view of an electrical connector according to an embodiment in a first configuration.
Figure 6:
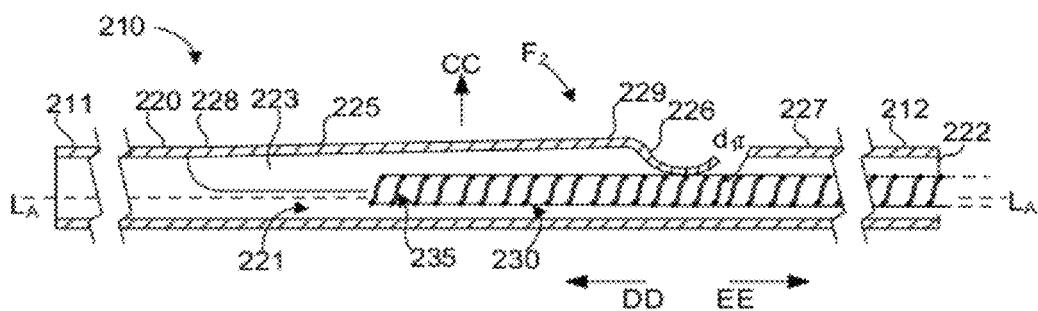
FIG. 6 is a cross-sectional view of the electrical connector shown in FIG. 5 and an electronic implant taken along line C-C in FIG. 7, in a second configuration.
Figure 7:
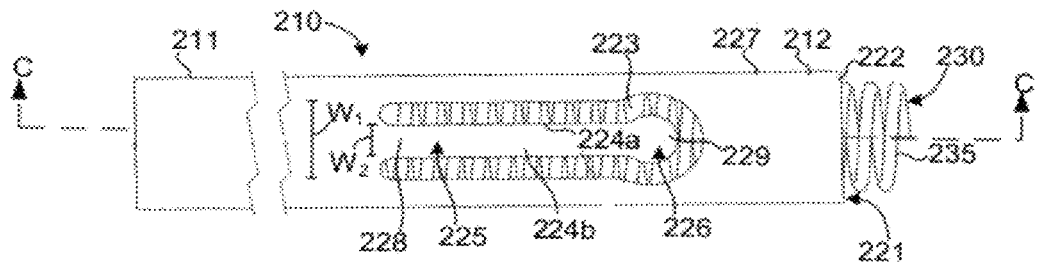
FIG. 7 is a top view of the electrical connector and the electronic implant shown in FIG. 6 in the second configuration.

FIGS. 5 and 6 are cross-sectional side views of an electrical connector 210 according to an embodiment in a first configuration and a second configuration, respectively. Additionally, FIG. 7 is a top view of the electrical connector 210. The electrical connector 210, which can be constructed of, for example, metal tubing, has a length $L_1$ and includes a distal end portion 212, a proximal end portion 211, and a side wall 220. The side wall 220 of the electrical connector 210 defines an elongate opening 223 and a lumen 221 having an opening 222 at the distal end portion 212 of the electrical connector 210. The lumen 221, which extends the entire length of the electrical connector 210, is configured to receive a portion of an electronic implant 230 via the opening 222. In some embodiments, the lumen 221 can be a blind hole such that the lumen 221 extends only through a portion of the electrical connector 210.

As shown in FIG. 7, the elongate opening 223 is a substantially U-shaped opening within the side wall 220 of the electrical connector 210. The elongate opening 223 has a length $L_2$ (see FIG. 5) and an overall width $W_1$ (see FIG. 7). Specifically, the elongate opening 223 is defined along a longitudinal axis $L_A$ of the electrical connector 210 between the proximal end portion 211 and the distal end portion 212 of the electrical connector 210. In this manner, the elongate opening 223 divides the side wall 220 into a first portion 225 and a second portion 227. Similarly stated, the elongate opening 223 forms the perimeter and/or boundary of the first portion 225 of the side wall 220. Said another way, the first portion 225 of the side wall 220 is the region bounded by the elongate opening 223.

The first portion 225 of the side wall 220, which has a length $L_3$ (see FIG. 5) and a width $W_2$ (see FIG. 7), has a proximal section 228, a distal section 229, a first side 224a and a second side 224b. The proximal section 228 of the first portion 225 forms a substantially continuous surface with the second portion 227 of the side wall 220. The distal section 229, the first side 224a and the second side 224b of the first portion 225 are spaced apart from the second portion 227 of the side wall 220. The distal section 229 of the first portion 225 includes a protrusion 226 having a substantially curved shape that is disposed within the lumen 221. In this manner, the protrusion 226 is configured to contact a conductive portion 235 of the electronic implant 230 when the electronic implant 230 is disposed within the lumen 221.

The first portion 225 and the protrusion 226 are monolithically constructed. In some embodiments, however, the first portion 225 and the protrusion 226 can be separately constructed and later coupled together. In some such embodiments, the first portion 225 and the second portion 226 can be coupled together by any suitable means, as described above.

The first portion 225 of the side wall 220 is configured to move relative to the second portion 227 of the side wall 220 between a first position (corresponding to the first configuration of the electrical connector 210) and a second position (corresponding to the second configuration of the electrical connector 210). As shown in FIG. 5, when the electrical connector 210 is in the first configuration (i.e., spaced apart from the electronic implant 230), the first portion 225 is in the first position. When the first portion 225 of the side wall 220 is in the first position, the first portion 225 is aligned with the second portion 227. Similarly stated, when the first portion 225 of the side wall 220 is in the first position, the first portion 225 is substantially parallel to the second portion 227 of the side wall 220 and/or the longitudinal axis $A_L$. When the first portion 225 of the side wall 220 is in the first position, a size (e.g., a diameter) of the lumen 221 is substantially constant throughout the length $L_3$ of the first portion 225 of the side wall 220. Although the first portion 225 is shown and described as being substantially aligned with the second portion 227 when the first portion 225 is in the first position, in other embodiments, the first portion 225 is not aligned with the second portion 227 when the first portion 225 is in the first position.

The electrical connector 210 can be moved into the second configuration when the electronic implant 230 is inserted within the lumen 221 via opening 222. Specifically, the electronic implant 230 is moved longitudinally in direction DD within the lumen 221 such that the protrusion 226 contacts at least a portion of the conductive portion 235 of the electronic implant 230, as shown in FIG. 6. As a result of the contact between the protrusion 226 and the conductive portion 235, the first portion 225 of the side wall 220 is moved from the first position into the second position. Specifically, the conductive portion 235 of the electronic implant 230 causes the proximal section 228 of the first portion 225 to bend, which forces the first portion 225 to move outward in a substantially radial direction as shown by the arrow CC. Said another way, when the electrical connector is moved into the second configuration, the first portion 225 of the side wall 220 moves a distance $d_1$ relative to the second portion 227 of the side wall 220. For example, in some embodiments, the first portion 225 can move approximately 0.13 mm in the substantially radial direction CC relative to the second portion 227 of the side wall 220. In this manner, the electrical connector 210 and the electronic implant 230 can be collectively coupled and placed in the second configuration.

Although the first portion 225 of the side wall 220 is illustrated and described above as being configured to move relative to the second portion 227 of the side wall 220 in the substantially radial direction as shown by the arrow CC in FIG. 6, in other embodiments, the first portion 225 can be configured to move relative to the second portion 227 in a direction that has a longitudinal component and a radial component. In some embodiments, the first portion 225 is configured to elastically deform when the first portion 225 moves from the first position to the second position, as described above. In other embodiments, the first portion 225 is configured to plastically deform when the first portion 225 moves from the first position to the second position, as described above.

When the electrical connector 210 is in the second configuration (which corresponds to the second position of the first portion 225 of the side wall 220), the electronic implant 230 is disposed within the lumen 221 such that the protrusion 226 contacts the conductive portion 235 of the electronic implant 230. As shown in FIG. 6, when the electrical connector 210 is in the second configuration, the first portion 225 of the side wall 220 is offset from and/or not aligned with the second portion 227 of the side wall 220. Similarly stated, when the electrical connector 210 is in the second configuration, the first portion 225 is angularly offset from (i.e., non-parallel to) the second portion 227 of the side wall 220 and/or the longitudinal axis $A_L$. When the electrical connector 210 is in the second configuration, the first portion 225 of the side wall 220 is spaced apart from the second portion 227 of the side wall 220 in the radial direction by the distance $d_1$.

When the electrical connector 210 is in the second configuration, the first portion 225 of the side wall 220 exerts a force $F_2$ on the conductive portion 235 of the electronic implant 230 via the protrusion 226. In this manner, when the electrical connector 210 is in the second configuration, movement of the electronic implant 230 relative to the electrical connector 210 is limited. Similarly stated, when the electrical connector 210 is in the second configuration, the electronic implant 230 is retained within the lumen 221 of the electrical connector 210. Moreover, as described in more detail below, the force $F_2$ exerted by the first portion 225 of the side wall 220 is sufficient to electrically couple the electronic implant 230 to the electrical connector 210. As a result of the electrical coupling between the protrusion 226 and the conductive portion 235, an electrical signal can be conveyed between the conductive portion 235 and the first portion 225 via the protrusion 226. In some embodiments, an external device (not shown) is coupled to the proximal end portion 211 of the electrical connector 210 such that an electrical signal can be conveyed between the external device and the electronic implant 230 via the first portion 225 and the protrusion 226.

The magnitude of the force $F_2$ can be any suitable value to retain the electronic implant 230 within the electrical connector 210 and/or to maintain an electrical coupling between the electronic implant 230 and the electrical connector 210. For example, in some embodiments, the first portion 225 of the side wall 220 can exert a force $F_2$ of between approximately 5 grams ($4.9 \times 10^{-2}$ N) and approximately 15 grams ($1.47 \times 10^{-1}$ N) on the conductive portion 235 of the electronic implant 235. The force $F_2$ exerted on the conductive portion 235 of the electronic implant 230 by the first portion 225 is insufficient to deform the conductive portion 235, as shown in FIG. 6. In this manner, the electronic implant 230 can be coupled to the electrical connector 210 without damaging the conductive portion 235. Moreover, this arrangement allows the electronic implant 230 to be repeatedly coupled to and decoupled from the electrical connector 210 without damaging the conductive portion 235.

The magnitude of the force $F_2$ can be any suitable value to limit longitudinal and/or rotational movement of the electronic implant 230 relative to the electrical connector 210. For example, in some embodiments, the magnitude of the force $F_2$ can be any suitable value to limit longitudinal movement of the electronic implant 230 relative to the electrical connector 210 in directions shown by the arrows DD and EE. For example, in some embodiments, the magnitude of the force $F_2$ can be such that longitudinal movement of the electronic implant 230 relative to the electrical connector 210 is prevented when a longitudinal force up to 2 grams ($1.96 \times 10^{-2}$ N) is exerted on the electronic implant 230. Similarly stated, in some embodiments, the magnitude of the force $F_2$ can be such that a pull-out force of greater than about 2 grams is required to remove the electronic implant 230 from the electrical connector 210.

In some embodiments, the magnitude of the force $F_2$ exerted on the conductive portion 235 of the electronic implant 230 by the first portion 225 of the side wall 220 is associated with a spring constant of the first portion 225. The spring constant can be any suitable value. For example, in some embodiments, the first portion 225 can have a spring constant between approximately 30 g/mm (0.294 N/mm) and approximately 40 g/mm (0.392 N/mm). In some embodiments, the spring constant of the first portion 225 can be a factor of the thickness $t_1$ of the side wall 220 of the first portion 225, the width of the first portion 225, the length $L_3$ of the first portion 225 and/or characterized by the properties of the material used to construct the first portion 225. For example, in some embodiments, the spring constant of the first portion 225 can be calculated using the following equation, $$K=(Et_1^3*W_2)/(4L_3^3)$$

where K is the spring constant of the first portion 225 and E is Young's modulus (i.e., the modulus of elasticity of the first portion 225). In some embodiments, the side wall 220 has a constant thickness $t_1$ such that the first portion 225 of the side wall 220 has a ratio of thickness $t_1$ to length $L_3$ of approximately 85:1.

Although the side wall 220 of the electrical connector 210 is illustrated and described above as having a constant thickness $t_1$, in some embodiments, the first portion 225 of the side wall 220 has a thickness greater than a thickness of the second portion 227 of the side wall 220. In other embodiments, the second portion 227 of the side wall 220 can have a thickness greater than the first portion 225 of the side wall 220. In some embodiments, the thickness $t_1$ of the side wall 220 can vary along the length $L_1$ of the electrical connector 210.

In some embodiments, the electrical connector 210 can be constructed from a conductive material. In this manner, the first portion 225, the second portion 227 and the protrusion 226 are electrically conductive. Such conductive materials can include, for example, titanium, pyrolytic carbon, stainless steel, platinum, iridium, carbon and any suitable combination thereof. In some embodiments, for example, the electrical connector 210 can be constructed from titanium plated with a layer of platinum, iridium, pyrolytic carbon, vapor deposited carbon, or the like to prevent oxidization of the titanium to improve the electrical conductivity of the first portion 225 and/or the protrusion 226. Furthermore, in some embodiments, the first portion 225 and the protrusion 226 can be constructed from different conductive materials. For example, the first portion 225 can be constructed from stainless steel and the protrusion 226 can be constructed from titanium. Similarly, the first portion 225 and the second portion 227 can be constructed from different conductive materials.

In some embodiments, the electrical connector 210 can include both electrically conductive materials and electrically insulative materials. For example, in some embodiments, the first portion 225 and/or the protrusion 226 can be constructed from an electrically conductive material while the second portion 227 can be constructed from an electrically insulative material such as, for example, a rigid epoxy, polycarbonate, silicone, polytetrafluroethylene, polypropylene, polyurethane and polysulfone (PSU).

Figure 8:
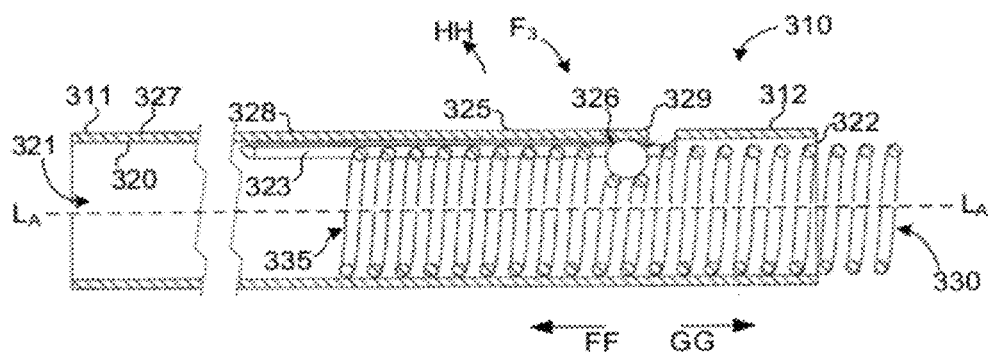
FIG. 8 is a cross-sectional view of an electrical connector and an electronic implant, according to an embodiment.

Although the electrical connector 210 is shown and described above as exerting a force $F_2$ on the electronic implant 230 such that the conductive portion 235 is substantially undeformed, in other embodiments, an electrical connector can be configured to exert a force on an electronic implant such that a portion of the electronic implant is deformed. For example, FIG. 8 is a cross-sectional side view of an electrical connector 310 according to an embodiment having an electronic implant 330 disposed therein. The electrical connector 310 includes a distal end portion 312, a proximal end portion 311 and a side wall 320. The side wall 320 of the electrical connector 310 defines an elongate opening 323 and a lumen 321 having an opening 322 at the distal end portion 312 of the electrical connector 310. The lumen 321, which extends therethrough, is configured to receive a portion of an electronic implant 330 via the opening 322, as discussed above. In some embodiments, the lumen 321 can be a blind hole such that the lumen 321 extends only through a portion of the electrical connector 310.

The elongate opening 323 is defined along a longitudinal axis $L_A$ of the electrical connector 310 between the proximal end portion 311 and the distal end portion 312 of the electrical connector 310. In this manner, the elongate opening 323 divides the side wall 320 into a first portion 325 and a second portion 327 such that the elongate opening 323 forms the perimeter of the first portion 325, as discussed above. In some embodiments, the elongate opening 323 can be a U-shaped cut-out within the side wall 320 of the electrical connector 310, as described above.

The first portion 325 of the side wall 320 has a proximal section 328, a distal section 329, a first side (not shown) and a second side (not shown). The proximal section 328 of the first portion 325 forms a substantially continuous surface with the second portion 327 of the side wall 320, and the distal section 329, the first side and the second side of the first portion 325 are spaced apart from the second portion 327. The distal section 329 of the first portion 325 is coupled to a protrusion 326 having a substantially spherical shape that is disposed within the lumen 321. The protrusion 326 is configured to contact a portion of a conductive portion 335 of the electronic implant 330.

The first portion 325 and the protrusion 326 are constructed from an electrically conductive material such that the first portion 325 is electrically coupled to the conductive portion 335 of the electronic implant 330 when the protrusion 326 contacts the conductive portion 335, as described above. In this manner, an electrical signal, which can be, for example, an electrical current, can be conveyed between the first portion 325 and the electronic implant 330.

The spherical protrusion 326 and the first portion 325 of the side wall 320 can be coupled together by any suitable means, as described above. In some embodiments, however, the spherical protrusion 326 and the first portion 325 of the side wall 320 can be monolithically constructed.

The first portion 325 of the side wall 320 is configured to move between a first position and a second position relative to the second portion 327 of the side wall 320, as described above with reference to the first portion 225 of the side wall 220 of the electrical connector 210. For example, the electrical connector 310 can be coupled to the electronic implant 330 (as shown in FIG. 8) by inserting the electronic implant 330 within the lumen 331 via opening 322. Specifically, the electronic implant 330 is moved longitudinally in direction FF within the lumen 321, as shown in FIG. 8. As a result of the contact between the protrusion 326 and the conductive portion 335, the first portion 325 can move relative to the first portion 327. Specifically, the conductive portion 335 of the electronic implant 330 causes the proximal end portion 328 of the first portion 325 to bend, which causes the first portion 325 to move outward in a substantially radial direction as shown by the arrow HH in FIG. 8.

When the electronic implant 330 is coupled to the electrical connector 310, the protrusion 326 contacts the conductive portion 335 of the electronic implant 330. When the electronic implant 330 is coupled to the electrical connector 310, the first portion 325 of the side wall 320 exerts a force $F_3$ on the conductive portion 335 of the electronic implant 330 via the protrusion 326. In this manner, when the electronic implant 330 is coupled to the electrical connector 310, movement of the electronic implant 330 relative to the electrical connector 310 is limited. Similarly stated, when the electronic implant 330 is coupled to the electrical connector 310, the electronic implant 330 is retained within the lumen 321 of the electrical connector 310. Moreover, the force $F_3$ exerted by the first portion 325 of the side wall 320 is sufficient to electrically couple the electronic implant 330 to the electrical connector 310. As a result of the electrical coupling between the protrusion 326 and the conductive portion 335, an electrical signal can be conveyed between the conductive portion 335 and the first portion 325 via the protrusion 326. In some embodiments, an external device (not shown) is coupled to the proximal end portion 311 of the electrical connector 310 such that an electrical signal can be conveyed between the external device and the electronic implant 330 via the first portion 325 and the protrusion 326.

As shown in FIG. 8, the magnitude of the force $F_3$ has a value sufficient to deform the conductive portion 335 of the electronic implant 330. The force $F_3$ can have any value sufficient to facilitate the elastic and/or plastic deformation of the conductive portion 335. In this manner, the force $F_3$ exerted on the conductive portion 335 can limit the movement of the electronic implant 330 relative to the electrical connector 310 and/or maintain an electrical coupling between the electronic implant 330 and the electrical connector 310, as described above. In some embodiments, the electrical connector 310 is configured to exert the force $F_3$ on the conductive portion 335 such that the conductive portion 335 deforms by a predetermined amount and/or in a controlled manner. In this manner, the electrical connector 310 can be configured to maintain the coupling with the electronic implant 330 without damaging the electronic implant 330. In some embodiments, the electrical connector 310 is configured to exert the force $F_3$ on the conductive portion 335 such that the conductive portion 335 deforms in the radial direction by an amount less than 0.13 mm.

In some embodiments, the magnitude of the force $F_3$ exerted on the conductive portion 335 of the electronic implant 330 by the first portion 325 of the side wall 320 is associated with a spring constant of the first portion 325 of the side wall 320. The spring constant can be any suitable value. For example, in some embodiments, the first portion 325 can have a spring constant between approximately 30 g/mm and approximately 40 g/mm. For example, in some embodiments, the spring constant of the first portion 325 can be a factor of a thickness of the side wall 320 of the first portion 325, a width of the first portion 325, a length of the first portion 325 and/or characterized by the properties of the material used to construct the first portion 325, as described above.

Although the spherical protrusion 326 is shown as being coupled to a distal-most portion of the first portion 325 of the side wall 320, in other embodiments, the spherical protrusion 326 can be coupled in any suitable location along the first portion 325 of the side wall 320. Additionally, in some embodiments, the spherical protrusion 326 can have any shape and/or size to facilitate contact with the conductive portion 335 of the electronic implant 330.

In some embodiments, the spherical protrusion 326 can facilitate the "scrubbing" of the conductive portion 335 of the electronic implant 330. Specifically, in some such embodiments, the spherical protrusion 326 exerts a force on the conductive portion 335 such that the spherical protrusion 326 removes impurities, such as, for example, oxidation, on the surface of the conductive portion 335 upon contact of the conductive portion 335. In this manner, the electrical conductivity of the conductive portion 335 is preserved and/or enhanced.

In some embodiments, the electrical connector 310 can be constructed from a conductive material. Such conductive materials can include, for example, titanium, pyrolytic carbon, stainless steel, platinum, iridium, carbon and any suitable combination thereof, as discussed above. Furthermore, in some embodiments, the first portion 325 and the protrusion 326 can be constructed from different conductive materials, as discussed above. Similarly, the first portion 325 and the second portion 327 can be constructed from different conductive materials. In some embodiments, the electrical connector 310 can include both electrically conductive materials and electrically insulative materials, as discussed above.

Figure 9:
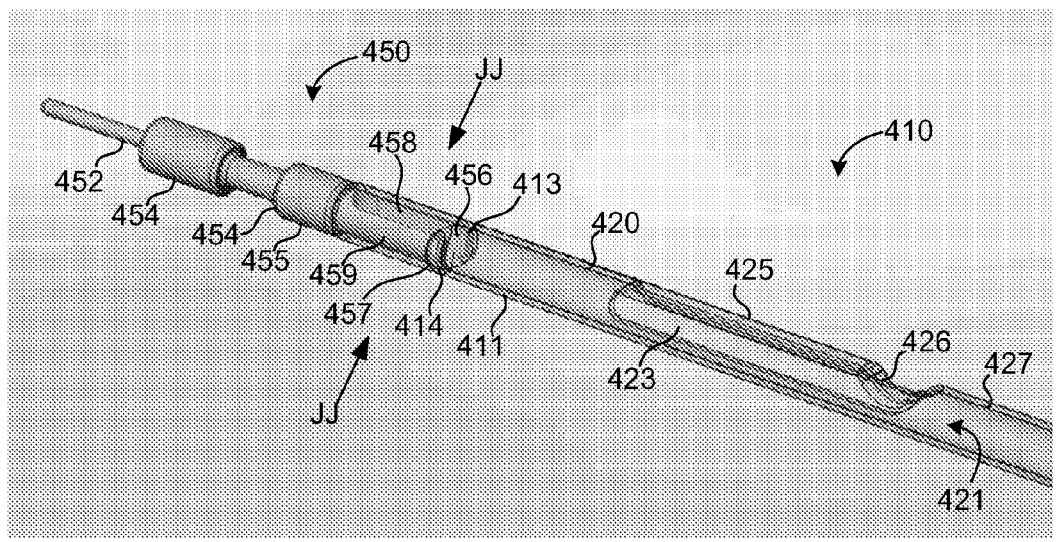
FIG. 9 is a perspective view of an electrical connector and a connection member according to an embodiment.

FIG. 9 is a perspective view of an electrical connector 410 and a connection member 450 according to an embodiment. The electrical connector 410 includes a distal end portion 412, a proximal end portion 411 and a side wall 420. The side wall 420 defines a lumen 421, an elongate opening 423 a first opening 413 and a second opening 414. The lumen 421, which extends the length of the electrical connector 410, has an opening (not shown) at the distal end portion 412 and an opening (not shown) at the proximal end portion 411, In this manner, a portion of an electronic implant can be disposed within the lumen 421 from the distal end portion 412 of the electrical connector 410 and a portion of the connection member 450 can be disposed within the lumen 421 from the proximal end portion 411 of the electrical connector 410. The elongate opening 423 divides the side wall 420 into a first portion 425 and a second portion 427, as described above. The first portion 425 of the side wall 420 includes a protrusion 426. The first portion 425 and the protrusion 426 have the same structure and operation as the first portion 225 and the protrusion 226 of the electrical connector 210, respectively, and are therefore not described in detail herein.

The first opening 413 defined by side wall 420 and the second opening 414 defined by side wall 420 are configured to receive a first protrusion 456 and a second protrusion 457 of the connection member 450. The first opening 413 and the second opening 414 are spaced approximately equidistant circumferentially about the proximal end portion 411 of the electrical connector 410. Similarly stated, the first opening 413 and the second opening 414 are disposed approximately 180 degrees apart.

Figure 10:
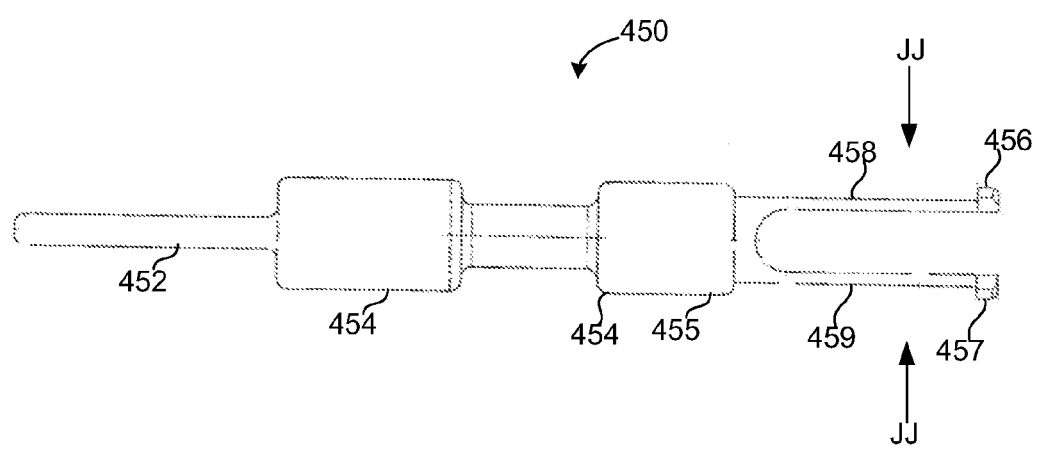
FIG. 10 is a top view of the connection member shown in FIG. 9.

The connection member 450 is disposed at the proximal end portion 411 of the electrical connector 410. FIG. 10 is a top view of the connection member 450, which includes a proximal end portion 452, a distal end portion 455 and two enlarged portions 454. The distal end portion 455 of the connection member 450 includes a first leg 458 and a second leg 459. The first leg 458 of the connection member 450 has a first protrusion 456 configured to be disposed within the first opening 413 defined by the side wall 420 of the electrical connector 410. Similarly, the second leg 459 of the connection member 450 has a second protrusion 457 configured to be disposed within the second opening 414 defined by the side wall 420 of the electrical connector 410.

The connection member 450 is configured to be removeably coupled to the electrical connector 410 via the first protrusion 456 and the second protrusion 457. Specifically, the first leg 458 and the second leg 459 are configured to be disposed within the lumen 421 defined by the side wall 420 to removeably couple the connection member 450 to the electrical connector 410. When the first protrusion 456 and the second protrusion 457 contact and/or engage the surface defining the lumen 421, the first leg 458 and the second leg 459 bend inward, as shown by arrows JJ. The first protrusion 456 and the second protrusion 457 are configured to be disposed within the first opening 413 and the second opening 414 defined by the side wall 420 such that the first leg 458 and the second leg 459 move back to their respective relaxed positions. In this manner, the connection member 450 is coupled to the electrical connector 410, and the first protrusion 456, the second protrusion 457, the first opening 413 and the second opening 414 cooperatively limit the axial and/or rotational movement of the connection member 450 relative to the electrical connector 410. In some embodiments, however, the connection member 450 does not include the first leg 458 and/or the second leg 459. In some such embodiments, the connection member 450 can be removably coupled to the electrical connector 410 via a press-fit.

In some embodiments, the connection member 450 and at least a portion of the electrical connector 410 are electrically conductive. In this manner, the connection member 450 is electrically coupled to the electrical connector 410 when the first protrusion 456 and the second protrusion 457 are disposed within the first opening 413 and the second opening 414 of the electrical connector 410. In some embodiments, the first portion 425 of the side wall 420 and the protrusion 426 are electrically conductive. In this manner, the protrusion 426 is electrically coupled to the connection member 450 when the first protrusion 456 and the second protrusion 457 releasably engage the first opening 413 and the second opening 414. In some such embodiments, the connection member 450 can be electrically coupled to an electronic implant (not shown) when the protrusion 426 is electrically coupled to a conductive portion (not shown) of the electronic implant, as described above. In this manner, an electrical signal, which can be, for example, an electrical current, can be conveyed between the connection member 450 and the electronic implant.

In some embodiments, the proximal end portion 452 of the connection member 450 is configured to be coupled to an external device (not shown). The external device can be, for example, an electrical stimulator. In this manner, the electrical connector 410 is operatively coupled to the external device via the connection member 450. As a result of the operative coupling between the electrical connector 410 and the external device, an electrical signal can be conveyed between the external device and the electrical connector 410. In some such embodiments, an electrical signal can be conveyed between the external device and an electronic implant when the electronic implant (not shown) is disposed within the lumen 421 of the electrical connector 410 and the protrusion 426 is electrically coupled to a conductive portion (not shown) of the electronic implant.

In some embodiments, the electrical connector 410 can be constructed from a conductive material, as discussed above. Furthermore, in some embodiments, the first portion 425 and the protrusion 426 can be constructed from different conductive materials, as discussed above. Similarly, the first portion 425 and the second portion 427 can be constructed from different conductive materials. In some embodiments, the electrical connector 410 can include both electrically conductive materials and electrically insulative materials, as discussed above.

In some embodiments, the connection member 450 can be constructed from a conductive material. In this manner, the first leg 458 and the second leg 459 are electrically conductive. Such conductive materials can include, for example, titanium, pyrolytic carbon, stainless steel, platinum, iridium, carbon and any suitable combination thereof. In some embodiments, for example, the connection member 450 can be constructed from titanium plated with a layer of platinum, iridium, pyrolytic carbon, vapor deposited carbon, or the like to prevent oxidization of the titanium to improve the electrical conductivity of the first leg 458 and the second leg 459. Furthermore, in some embodiments, the first leg 458 and the second leg 459 can be constructed from different conductive materials. For example, the first leg 458 can be constructed from stainless steel and the second leg 459 can be constructed from titanium. Similarly, the proximal end portion 452 and the distal end portion 455 can be constructed from different conductive materials.

In some embodiments, the connection member 450 can include both electrically conductive materials and electrically insulative materials. For example, in some embodiments, the proximal end portion 452 and/or the distal end portion 455 can be constructed from an electrically conductive material while the enlarged portions 454 can be constructed from an electrically insulative material such as, for example, a rigid epoxy, polycarbonate, silicone, polytetrafluroethylene, polypropylene, polyurethane and polysulfone (PSU).

Although the electrical connector 410 and the connection member 450 are illustrated and described above as being removeably coupled together via the first protrusion 456 and the second protrusion 457, in some embodiments, the electrical connector 410 and the connection member 450 can be coupled together by any suitable means. In some embodiments, for example, the electrical connector 410 and the connection member 450 can be coupled together by a mechanical coupling (e.g., an interference fit, detents, a threaded coupling, or the like), an electronic coupling (e.g., a magnetic coupling) and/or a chemical bond. For example, in some embodiments, the electrical connector 410 and the connection member 450 can be coupled together via a press-fit. In some embodiments, however, the electrical connector 410 and the connection member 450 can be monolithically constructed.

Although the connection member 450 is illustrated and described as being coupled to the proximal end portion 411 of the electrical connector 410, in some embodiments, the connection member 450 can be coupled at any location along the electrical connector 410.

Figure 11:
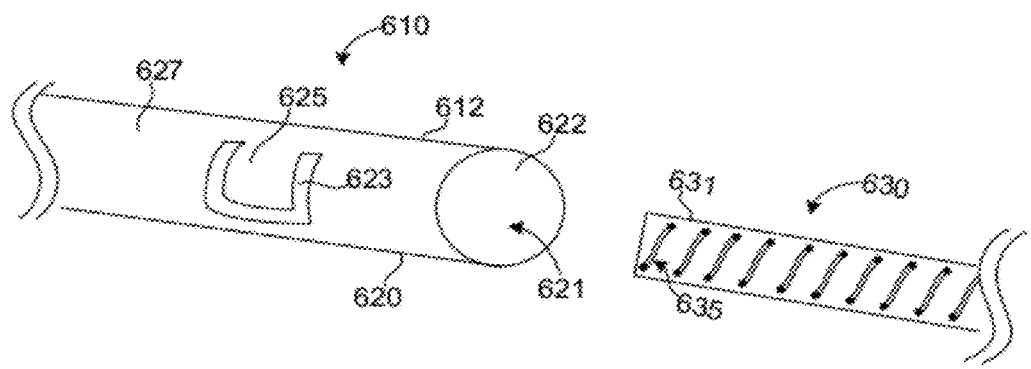
FIG. 11 is a perspective view of an electrical connector and an electronic implant according to an embodiment in a first configuration.
Figure 12:
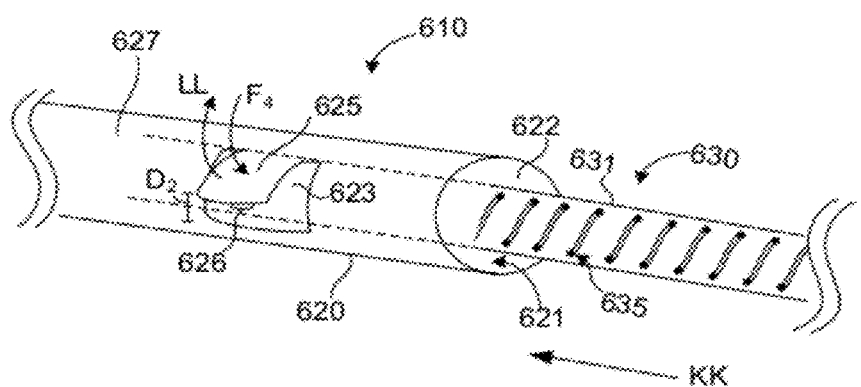
FIG. 12 is a perspective view of the electrical connector and the electronic implant shown in FIG. 11 in a second configuration.

Although the electrical connectors are described and illustrated above as having a longitudinal elongate opening, in some embodiments, the elongate opening can be in any orientation. For example, FIGS. 11 and 12 show an electrical connector 610 defining an elongate opening 623 having a circumferential orientation according to an embodiment in a first configuration and a second configuration, respectively. The electrical connector 610 includes a side wall 620 that defines a lumen 621 and an elongate opening 623. The lumen 621, which has a substantially circular cross-section, has an opening 622 at the distal end portion 612 of the electrical connector 610, as described above. The lumen 621 is configured to receive a portion of an electronic implant 630 via the opening 622, as described above.

As shown in FIG. 11, the elongate opening 623 is a substantially U-shaped opening within the side wall 620. Specifically, the elongate opening 623 is defined in a circumferential direction about the distal end portion 612 of the electrical connector 610. In this manner, the elongate opening 623 divides the side wall 620 into a first portion 625 and a second portion 627. Similarly stated, the elongate opening 623 forms the perimeter and/or boundary of the first portion 625 of the side wall 620, as described above. The first portion 625 of the side wall 620 includes a protrusion 626 (shown in FIG. 12) that is disposed within the lumen 621. The protrusion 626 is configured to contact a conductive portion 635 of the electronic implant 630 when the conductive portion 635 is disposed within the lumen 621, as described above.

The first portion 625 of the side wall 620 is configured to move relative to the second portion 627 of the side wall 620 between a first position (FIG. 11) and a second position (FIG. 12). Specifically, at least the first portion 625 of the side wall 620 is flexible such that the first portion 625 can move, bend and/or deform between the first position and the second position, as described above. As shown in FIG. 11, when the electrical connector 610 is in the first configuration (i.e., spaced apart from the electronic implant 630), the first portion 625 is in the first position. In the first position, the first portion 625 is aligned with the second portion 627, in a manner similar to that described above with reference to the electrical connector 210. In other embodiments, the first portion 625 is not aligned with the second portion 627 when the first portion 625 is in the first position.

The electrical connector 610 can be moved into the second configuration when the electronic implant 630 is inserted within the lumen 621 via opening 622. Specifically, the electronic implant 630 is moved longitudinally in direction KK within the lumen 621, as shown in FIG. 12 such that the protrusion 626 contacts the conductive portion 635 of the electronic implant 630. As a result of the contact between the protrusion 626 and the conductive portion 635, the first portion 625 moves into the second position. Specifically, the conductive portion 635 of the electronic implant 630 causes the first portion 625 to bend, which forces the first portion 625 to move outward in a substantially radial direction LL. For example, in some embodiments, the first portion 625 can be configured to move approximately 0.13 mm in the substantially radial direction LL relative to the second portion 627 of the side wall 620. In this manner, the electrical connector 610 and the electronic implant 630 can be collectively coupled and placed in the second configuration.

In some embodiments, the first portion 625 is configured to elastically deform when the first portion 625 moves from the first position to the second position, as described above. In other embodiments, the first portion 625 is configured to plastically deform when the first portion 625 moves from the first position to the second position, as described above.

The first portion 625 of the side wall 620 exerts a force $F_4$ on the conductive portion 635 of the electronic implant 630 via the protrusion 626, as described above. In some embodiments, the force $F_4$ exerted on the conductive portion 635 by the first portion 625 can be sufficient to limit the movement of the electronic implant 630 relative to the electrical connector 610 and/or to maintain the electrical coupling between the electrical connector 610 and the electronic implant 630. In some embodiments, the force $F_4$ exerted on the conductive portion 635 of the electronic implant 630 by the first portion 625 is insufficient to deform the conductive portion 635. In other embodiments, however, the force $F_4$ that the first portion 625 of the side wall 620 exerts on the conductive portion 635 of the electronic implant 630 is sufficient to elastically deform the conductive portion 635.

In some embodiments, the magnitude of the force $F_4$ exerted on the conductive portion 635 of the electronic implant 630 by the first portion 625 of the side wall 620 is associated with a spring constant of the first portion 625, as described above.

Figure 13:
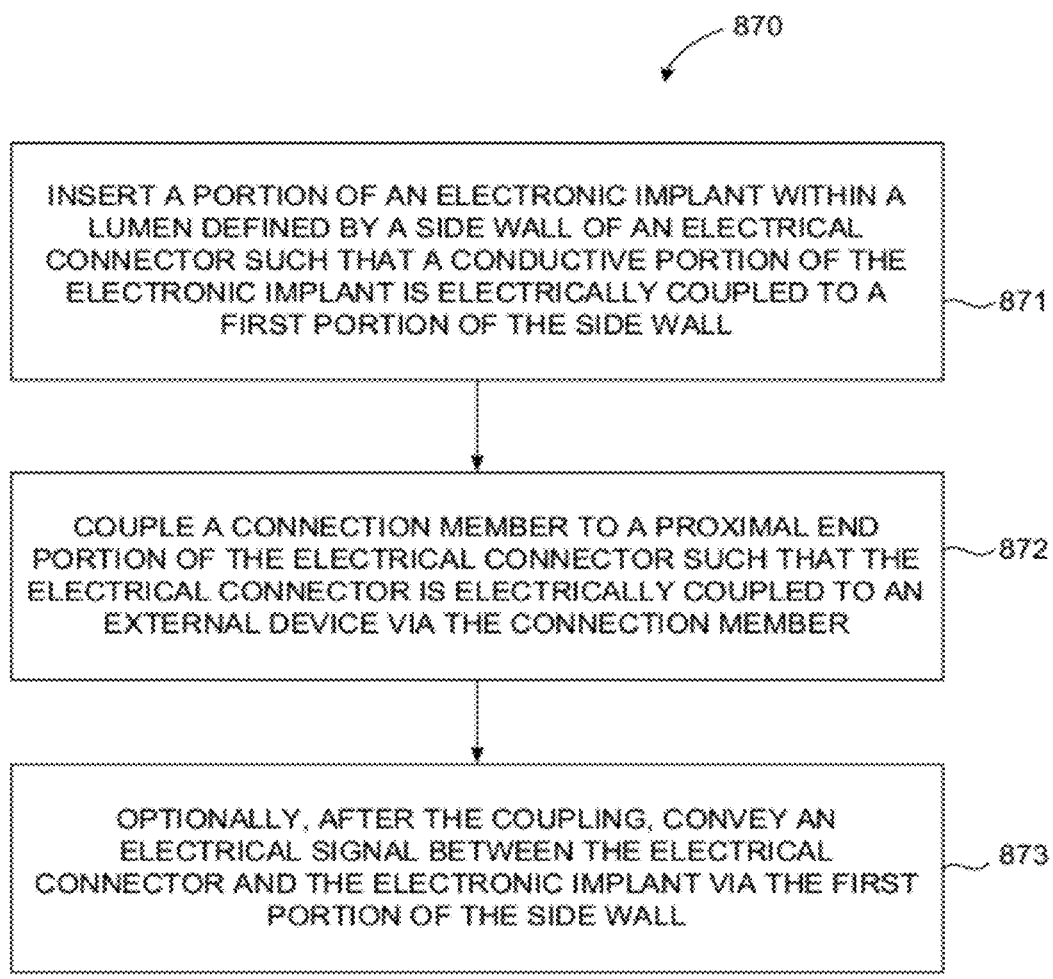
FIG. 13 is a flow chart of a method according to an embodiment.

FIG. 13 is a flow chart of a method 870 of coupling an electrical connector to an electronic implant according to an embodiment. The method 870 includes inserting a portion of an electronic implant within a lumen defined by a side wall of the electrical connector such that a conductive portion of the electronic implant is electrically coupled to a first portion of the side wall, 871. The side wall defines an elongate opening that divides the side wall into the first portion and a second portion. The first portion of the side wall is configured to plastically and/or elastically deform between a first position and a second position when the conductive portion is disposed within the lumen defined by the side wall. The electrical connector and the electronic implant can be any of the electrical connectors and electronic implants, respectively, shown and described herein.

In some embodiments, the inserting includes elastically deforming at least the conductive portion of the electronic implant via a protrusion disposed on the first portion of the side wall of the electrical connector when the protrusion is electrically coupled to the conductive portion of the electronic implant. In some embodiments, the inserting includes elastically deforming the first portion of the electrical connector such that the first portion is configured to move approximately 0.13 mm in a radial direction relative to the second portion of the side wall when the first portion moves from the first position to the second position.

The method includes coupling a connection member to a proximal end portion of the electrical connector such that the electrical connector is electrically coupled to an external device via the connection member, 872. In some embodiments, the coupling includes disposing a first protrusion and a second protrusion of the connection member within a first opening and a second opening defined by the proximal end portion of the electrical connector. In some embodiments, after the coupling, the method can further include conveying an electrical signal between the electrical connector and the electronic implant via the first portion of the side wall, 873.

While various embodiments have been described above, it should be understood that they have been presented by way of example only, and not limitation. Where methods described above indicate certain events occurring in certain order, the ordering of certain events may be modified. Additionally, certain of the events may be performed concurrently in a parallel process when possible, as well as performed sequentially as described above. Thus, the breadth and scope should not be limited by any of the above-described embodiments. While certain embodiments have been particularly shown and described, it will be understood that various changes in form and details may be made.

For example, although the electrical connector 210 is shown and described above as being configured to exert a force $F_2$ on the conductive portion 235 of the electronic implant 230 without substantially deforming the electronic implant 230, in other embodiments, the electrical connector 210 can be configured to exert a force on the electronic implant sufficient to elastically and/or plastically deform the conductive portion 235.

In some embodiments, the electrical connector can be a portion of an insertion tool such that the electrical connector can be configured to insert the electronic implant into a body. In some embodiments, the electrical connector can be any suitable shape and/or size to facilitate percutaneous insertion of the electrical connector within the body. For example, the electrical connector can have a cylindrical shape and a diameter of approximately 1 millimeter. In some embodiments, the electrical connector can be used during an open surgery and can be any suitable size and/or shape to facilitate such insertion.

In some embodiments, the first portion and the second portion of the side wall of the electrical connector can be monolithically constructed. In some embodiments, however, the first portion and the second portion of the side wall can be coupled together by a mechanical coupling (e.g., an interference fit, detents, a threaded coupling, a hinged coupling, or the like), an electronic coupling (e.g., a magnetic coupling) and/or a chemical bond.

In some embodiments, the first portion of the side wall of the electrical connector does not include a protrusion such that the first portion can be configured to contact the conductive portion of the electronic implant. In this manner, the first portion of the side wall is electrically coupled to the conductive portion of the electronic implant directly.

Although the electrical connectors are described and illustrated above as having a first portion configured to move between a first position and a second position when then protrusion of the first portion contacts the conductive portion of the electronic implant, in some embodiments, the electrical connector can include a protrusion configured to move between a first position and a second position when the protrusion contacts the conductive portion of the electronic implant. In some such embodiments, the protrusion can be configured to plastically deform and/or elastically deform when the protrusion contacts the conductive portion of the electronic implant.

Although the electrical connectors are described and illustrated above as having an elongate opening configured to divide the side wall into a first portion and a second portion, in some embodiments, the electrical connector can have a side wall divided into a first portion and a second portion by another means other than an elongate opening. For example, the side wall of the electrical connector can be divided along a longitudinal axis such that the first portion forms the first half of the electrical connector and the second portion forms the second half of the electrical connector. In some such embodiments, the first portion of the side wall can be hinged to the second portion of the side wall such that the electrical connector has a clam-shell configuration. In this manner, the electrical connector can be configured to close around the electronic implant (i.e., clamp the electronic implant) when the electronic implant is disposed within a lumen defined by the first portion and second portion. Moreover, this arrangement allows the electronic implant to be inserted within the electrical connector when the hinged portion is in a first (or opened) position, thereby minimizing the contact between the electrical connector and the electronic implant during the insertion process. After the electronic implant is within the electrical connector, the hinged portion can be closed to and electrically coupled to the electronic implant.

Although various embodiments have been described as having particular features and/or combinations of components, other embodiments are possible having a combination of any features and/or components from any of embodiments where appropriate. For example, in some embodiments, the connection member 450 can be releasably coupled to the proximal end portion 311 of the electrical connector 310 having a spherical protrusion 326.

What is claimed is:

1. An apparatus, comprising:
an electrical connector having a proximal end portion defining a first opening and a second opening each circumferentially disposed about the electrical connector, the connector having a side wall defining a lumen configured to receive at least a conductive portion of an electronic implant, the side wall defining an elongate opening such that the side wall is divided into a first portion and a second portion, the second portion of the side wall defining an outer circumference, the first portion of the side wall configured to move relative to the second portion of the side wall between a first position and a second position, the first portion of the side wall being displaced outside of the outer circumference of the second portion of the sidewall when in the second position,
the first portion of the side wall being electrically conductive and including a protrusion configured to contact the conductive portion of the electronic implant such that the conductive portion of the electronic implant is electrically coupled to the first portion of the side wall when the first portion of the side wall is in the second position; and
a connection member having a first protrusion and a second protrusion, the first protrusion and the second protrusion configured to releasably engage the first opening and the second opening of the electrical connector such that the connection member is electrically coupled to the electrical connector.

2. The apparatus of claim 1, wherein the protrusion and the first portion of the side wall are monolithically constructed.

3. The apparatus of claim 1, wherein the electrical connector is configured to convey an electrical signal between the electronic implant and an electronic device via the first portion of the side wall when the protrusion is electrically coupled to the conductive portion of the electronic implant.

4. The apparatus of claim 1, wherein the protrusion is configured to elastically deform at least the conductive portion of the electronic implant when the protrusion is electrically coupled to the conductive portion of the electronic implant.

5. The apparatus of claim 1, wherein the first portion of the side wall is configured to one of plastically deform and elastically deform when the first portion of the side wall is moved between the first position and the second position.

6. The apparatus of claim 1, wherein the first portion of the side wall exerts a force between approximately $4.9 \times 10^{-2}$ N and approximately $1.47 \times 10^{-1}$ N on the conductive portion of the electronic implant when the protrusion is electrically coupled to the conductive portion of the electronic implant.

7. The apparatus of claim 1, wherein the electrical connector is a portion of an insertion tool, the insertion tool configured to insert a portion of the electronic implant within a body.

8. The apparatus of claim 1, wherein the first portion of the side wall exerts a force on the electronic implant when the first portion of the side wall is in the second position such that movement of the electronic implant relative to the electrical connector is limited.

9. The apparatus of claim 1, wherein the first portion of the side wall exerts a radial force on the electronic implant such that when a longitudinal force up to $1.96 \times 10^{-2}$ N is exerted on the electronic implant, longitudinal movement of the electronic implant relative to the electrical connector is prevented.

10. An apparatus, comprising:
an electrical connector having a side wall defining a lumen configured to receive at least a conductive portion of an electronic implant, the side wall defining an elongate opening such that the side wall is divided into a first portion and a second portion, the first portion of the side wall being substantially surrounded by the opening,
the first portion configured to one of plastically deform and elastically deform when the first portion is moved relative to the second portion between a first position and a second position, the first portion configured to move from the first position to the second position when the conductive portion of the electronic implant is positioned adjacent the first portion, the first portion configured to exert a force between approximately $4.9 \times 10^{-2}$ N and approximately $1.47 \times 10^{-1}$ N on the conductive portion of the electronic implant when the first portion is in the second position and in contact with the conductive portion of the electronic implant; the first portion of the side wall has a spring constant of between approximately 0.294 N/mm and approximately 0.392 N/mm.

11. The apparatus of claim 1, wherein the protrusion of the first portion of the side wall is configured to move approximately 0.13 mm in a radial direction relative to the second portion of the side wall when the first portion moves from the first position to the second position.

12. The apparatus of claim 1, wherein the first portion of the side wall has a spring constant of between approximately 0.294 N/mm and approximately 0.392 N/mm.

13. A method, comprising:
inserting a portion of an electronic implant within a lumen defined by a side wall of an electrical connector such that a conductive portion of the electronic implant is electrically coupled to a first portion of the side wall, the side wall defining an elongate opening such that the side wall is divided into the first portion and a second portion, the first portion of the side wall configured to one of plastically deform and elastically deform between a first position and a second position when the conductive portion is disposed within the lumen, at least a portion of the first portion of the side wall being displaced outside of an outer circumference defined by the second portion of the side wall when the first portion of the side wall is in the second position; and
coupling a connection member to a proximal end portion of the electrical connector such that the electrical connector is electrically coupled to an external device via the connection member, a first protrusion and a second protrusion of the connection member being disposed within a first opening and a second opening defined by the proximal end portion of the electrical connection when the connection member is coupled to the proximal end portion of the electrical connector.

14. The method of claim 13, wherein the inserting includes elastically deforming the first portion of the electrical connector such that the first portion is configured to move approximately 0.13 mm in a radial direction relative to the second portion of the side wall when the first portion moves from the first position to the second position.

15. The apparatus of claim 10, wherein the first portion of the side wall includes a protrusion configured to electrically couple the first portion to the conductive portion of the electronic implant when the first portion is in the second position.

16. The apparatus of claim 10, wherein the first portion of the side wall is configured to elastically deform at least a conductive portion of the electronic implant when the first portion is in contact with the conductive portion of the electronic implant.

17. The apparatus of claim 10, wherein the force prevents the electronic implant from moving relative to the electrical connector.

18. The apparatus of claim 10, wherein the first portion of the side wall is configured to move up to approximately 0.13 mm in a radial direction relative to the second portion of the side wall when the first portion moves from the first position to the second position.

19. The method of claim 13, further comprising:
after the coupling, conveying an electrical signal between the electrical connector and the electronic implant via the first portion of the side wall.

20. The apparatus of claim 10, wherein the first portion of the side wall has a ratio of a thickness of the first portion of the side wall to a length of the first portion of the side wall of approximately 85:1.

21. The method of claim 13, wherein the inserting includes elastically deforming at least the conductive portion of the electronic implant via a protrusion disposed on the first portion of the side wall of the electrical connector when the protrusion is electrically coupled to the conductive portion of the electronic implant.

* * * * *